United States Patent

Chalmers

[11] 3,956,310
[45] May 11, 1976

[54] N-CARBAMOYL IMIDAZOLIDINONES AND IMIDAZOLIDINETHIONES

[75] Inventor: Alexander Michael Chalmers, Cheadle, England

[73] Assignee: Ciba-Geigy Corporation, Ardsley, N.Y.

[22] Filed: Jan. 9, 1975

[21] Appl. No.: 539,376

[30] Foreign Application Priority Data
Jan. 12, 1974 United Kingdom............... 1550/74

[52] U.S. Cl................ 260/309.7; 260/45.8 N; 204/159.18; 204/162 R
[51] Int. Cl.²................................ C07D 49/34
[58] Field of Search ................... 260/309.7

[56] References Cited
UNITED STATES PATENTS

| | | | |
|---|---|---|---|
| 3,248,398 | 4/1966 | Mühlbauer et al. | 260/309.7 X |
| 3,532,703 | 10/1970 | Murayama et al. | 260/309.7 X |
| 3,799,942 | 3/1974 | Boocock et al. | 260/309.7 X |

*Primary Examiner*—Ethel G. Love
*Attorney, Agent, or Firm*—Nestor W. Shust

[57] ABSTRACT

Compounds having the formula

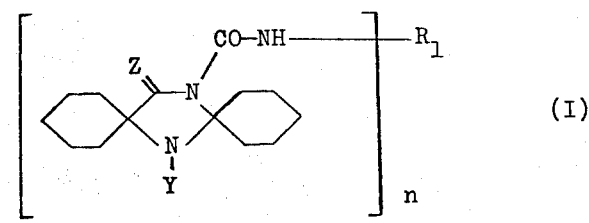

as well as salts thereof, wherein $n$ is 1 or 2, Y is O, hydrogen or a straight- or branched chain alkyl residue having from 1 to 4 carbon atoms Z is O or S and when $n$ is 1, $R_1$ is a substituted or unsubstituted hydrocarbyl residue having from 1 to 20 carbon atoms and when $n$ is 2, $R_1$ is a substituted or unsubstituted hydrocarbyl residue having from 2 to 20 carbon atoms, are suitable as stabilisers of organic material.

11 Claims, No Drawings

N-CARBAMOYL IMIDAZOLIDINONES AND IMIDAZOLIDINETHIONES

The present invention relates to new chemical compounds and, in particular to new N-carbamoyl imidazolidinones and imidazolidinethiones, processes for their production and their use as stabilisers for organic material.

According to the present invention, there are provided compounds having the formula

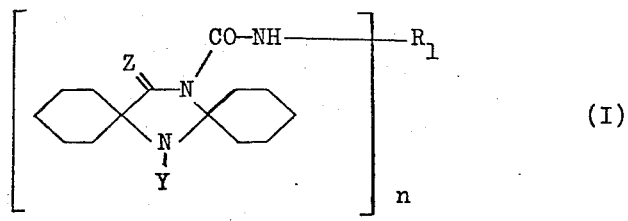

as well as salts thereof, wherein $n$ is 1 or 2, Y is hydrogen or a straight- or branched- chain alkyl residue having from 1 to 4 carbon atoms, Z is O or S and when $n$ is 1, $R_1$ is a substituted or unsubstituted hydrocarbyl residue having from 1 to 20 carbon atoms and when $n$ is 2, $R_1$ is a substituted or unsubstituted hydrocarbyl residue having from 2 to 20 carbon atoms.

A preferred sub-group of compounds falling within the definition of formula I are those having the formula

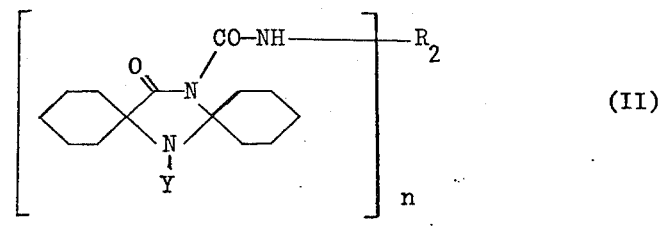

wherein Y and $n$ have their previous significance and, when $n$ is 1, $R_2$ is a straight- or branched chain alkyl residue having from 1 to 20 carbon atoms, a straight- or branched chain alkenyl residue having from 3 to 18 carbon atoms, a substituted or unsubstituted cycloalkyl residue having from 5 to 14 carbon atoms, a substituted or unsubstituted aryl residue having from 6 to 10 carbon atoms or an aralkyl residue having from 7 to 18 carbon atoms and when $n$ is 2, $R_2$ is a straight- or branched alkylene residue having from 2 to 20 carbon atoms, a substituted or unsubstituted arylene residue having from 6 to 10 carbon atoms or an aralkylene residue having from 7 to 18 carbon atoms. Suitable substituents on cycloalkyl or aryl residues $R_2$ are halogen atoms or alkyl groups having from 1 to 12 carbon atoms or alkoxy groups having from 1 to 4 carbon atoms.

A less preferred sub-group of compounds falling within the definition of formula I are those having the formula

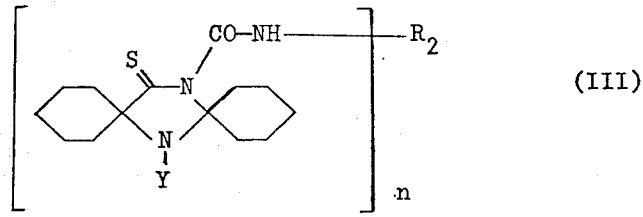

wherein Y, $R_2$ and $n$ have their previous significance.

Examples of substituents Y, apart from hydrogen and O are methyl, ethyl, n-propyl and n-butyl. Preferably the substituent Y is hydrogen.

When $n$ is 1, examples of substituents $R_1$ and $R_2$ in formulae I, II and III respectively are methyl, ethyl, n-propyl, isopropyl, n-butyl, sec-butyl, t-butyl, n-pentyl, 2-ethyl pentyl, 2-methylpentyl, n-octyl, 2,2,4-trimethyl pentyl, n-decyl, n-dodecyl, n-tetradecyl, n-octadecyl, n-eicosyl, allyl, n-decenyl, oleyl, n-octadecenyl, cyclopentyl, cyclohexyl, methylcyclohexyl, t-butyl cyclohexyl, t-octylcyclohexyl, cyclododecenyl, 1- or 2-perhydronaphthyl, adamantyl, cyclopentylmethyl, cyclohexylmethyl, β-cyclohexylethyl, phenyl, o-, m- and p-tolyl, 2,4- or 2,6-xylyl, mesityl, p-chlorophenyl, 3-chloro-p-tolyl, o-ethylphenyl, p-t-butylphenyl, 2,3- or 2,5-dichlorophenyl, 2,4- or 2,5-dimethoxy phenyl, α or β-naphthyl, p-n-octylphenyl and p-n-dodecylphenyl residues.

Preferred monovalent substituents $R_1$ and $R_2$ are alkyl residues such as methyl, ethyl, isopropyl, sec-butyl, 2-ethylhexyl, n-dodecyl and n-octadecyl residues, aryl groups, especially phenyl, and aralkyl residues, especially those having from 7 to 12 carbon atoms, e.g. benzyl.

When $n$ is 2, $R_1$ and $R_2$ may be a 1,2-ethylene, 1,4-n-butylene, 1,6-n-hexylene, 2,2,4-trimethyl-1,6-n-hexylene, 1,10-n-decylene, 1,20-n-eicosylene, 2,4-tolylene, 4,4′-diphenylenemethane or 4,4′-diphenylene- 1″,6″-n-hexylene residue.

Preferred divalent residues $R_1$ and $R_2$ are alkylene residues having from 2 to 6 carbon atoms and aralkylene residues having from 7 to 13 carbon atoms, and arylene with 6 to 12 carbon atoms, e.g. phenylene and naphthylene, biphenylyl and diphenylenemethane.

Examples of salts of the compounds of formula I include salts of inorganic acids such as phosphates, carbonates, sulphates, chlorides and salts of organic acids such as acetates, stearates, maleates, citrates, tartrates, oxalates, benzoates and substituted carbamic acids.

Examples of specific carbamoyl imidazolines of formula I are given in the following list:

14-methylcarbamoyl-7,14-diazadispiro[5.1.5.2]pentadecan-15-one
14-ethyl carbamoyl-7,14-diazadispiro[5.1.5.2]pentadecan-15-one
14-n-propyl carbamoyl-7,14-diazadispiro[5.1.5.2-]pentadecan-15-one
14-isopropyl carbamoyl-7,14-diazadispiro[5.1.5.2-]pentadecan-15-one
14-n-butyl carbamoyl-7,14-diazadispiro[5.1.5.2-]pentadecan-15-one
14-n-hexyl carbamoyl-7,14-diazadispiro[5.1.5.2-]pentadecan-15-one
14-(2'-ethylhexyl)carbamoyl-7,14-diazadispiro[5.1.5.2]pentadecan-15-one
14-n-dodecyl carbamoyl-7,14-diazadispiro[5.1.5.2-]pentadecan-15-one
14-n-eicosyl carbamoyl-7,14-diazadispiro[5.1.5.2-]pentadecan-15-one
14-allyl carbamoyl-7,14-diazadispiro[5.1.5.2]pentadecan-15-one
14-n-decenyl carbamoyl-7,14-diazadispiro[5.1.5.2-]pentadecan-15-one
14-n-octadecenyl carbamoyl-7,14-diazadispiro[5.1.5.2]pentadecan-15-one
14-cyclopentyl carbamoyl-7,14-diazadispiro[5.1.5.2-]pentadecan-15-one
14-cyclohexyl carbamoyl-7,14-diazadispiro[5.1.5.2-]pentadecan-15-one
14-cyclododecyl carbamoyl-7,14-diazadispiro[5.1.5.2]pentadecan-15-one
14-phenyl carbamoyl-7,14-diazadispiro[5.1.5.2]pentadecan-15-one
14-(2',4'-dimethoxyphenyl)-carbamoyl-7,14-diazadispiro[5.1.5.2]pentadecan-15-one
14-p-chlorophenyl carbamoyl-7,14-diazadispiro[5.1.5.2]pentadecan-15-one
14-o-tolyl carbamoyl-7,14-diazadispiro[5.1.5.2]pentadecan-15-one
14-(2',4'-xylyl)carbamoyl-7,14-diazadispiro[5.1.5.2]penta-15-one
14-α-naphthyl carbamoyl-7,14-diazadispiro[5.1.5.2]pentadecan-15-one
14-p-t-butylphenyl carbamoyl-7,14-diazadispiro[5.1.5.2]pentadecan-15-one
14-p-n-dodecylphenyl carbamoyl-7,14-diazadispiro[5.1.5.2]pentadecan-15-one
7-methyl-14-methyl carbamoyl-7,14-diazadispiro[5.1.5.2]pentadecan-15-one
7-oxyl-14-phenyl carbamoyl-7,14-diazadispiro[5.1.5.2]pentadecan-15-one
7-n-butyl-14-ethylcarbamoyl-7,14-diazadispiro[5.1.5.2]pentadecan-15-one
7-n-propyl-14-o-tolyl carbamoyl-7,14-diazadispiro[5.1.5.2]pentadecan-15-one
7-sec-butyl-14-cyclohexyl-7,14-diazadispiro[5.1.5.2-]pentadecan-15-one
7-isopropyl-14-cycloheptylcarbamoyl-7,14-diazadispiro[5.1.5.2]pentadecan-15-one
7-sec-butyl-14-n-hexyl carbamoyl-7,14-diazadispiro[5.1.5.2]pentadecan-15-one
7-oxyl-14-n-decyl carbamoyl-7,14-diazadispiro[5.1.5.2]pentadecan-15-one
ethane-1',2'-bis[14-carbamoyl-7,14-diazadispiro[5.1.5.2]pentadecan-15-one]
n-hexane-1',6'-bis[14-carbamoyl-7,14-diazadispiro[5.1.5.2]pentadecan-15-one]
2',2',4'-trimethylhexane-1',6'-bis[14-carbamoyl-7,14-diazadispiro[5.1.5.2]pentadecan-15-one]
n-eicosane-1',2'-bis[14-carbamoyl-7,14-diazadispiro[5.1.5.2]pentadecan-15-one
tolylene-2',4'-bis[14-carbamoyl-7,14-diazadispiro[5.1.5.2]pentadecan-15-one]
diphenylene methane-4',4''-bis[14-carbamoyl-7,14-diazadispiro[5.1.5.2]pentadecan-15-one]
[p,p-diphenylenehexane-1',6']-4'',4'''-[14-carbamoyl-7,14-diazadispiro[5.1.5.2]pentadecan-15-one]
1-[15'-oxo-7',14'-diazadispiro[5.1.5.2]pentadecyl-14'-carbonylamino]-3,5,5-trimethyl-3-[15''-oxo-7'',14''-diazadispiro[5.1.5.2]pentadecyl-4''-carbonyl amino methylene] cyclohexane
ethylene-1',2'-bis[14-carbamoyl-7-oxyl-7,14-diazadispiro[5.1.5.2]pentadecan-15-one]
n-hexylene-1',6'-bis[14-carbamoyl-7-n-butyl-7,14-diazadispiro[5.1.5.2]pentadecan-15-one]
diphenylenemethane-4',4''-bis[14-carbamoyl-7-sec-butyl-7,14-diazadispiro[5.1.5.2]pentadecan-15-one]
tolylene-2',4'-bis[14-carbamoyl-7-n-propyl-7,14-diazadispiro[5.1.5.2]pentadecan-15-one]
naphthylene-1',5'-bis[14-carbamoyl-7,14-diazadispiro[5.1.5.2]pentadecan-15-one]
3,3'-dimethoxybiphenylyl-4,4'-bis[14-carbamoyl-7,14-diazadispiro[5.1.5.2]-pentadecan-15-one].

The counterparts to the compounds listed above but having sulphur in the 15-position are also to be understood as being examples of specific compounds of formula I.

According to the present invention, there is also provided a process in which there is produced a compound of formula I, comprising reacting a 7,14-diazadispiro[5.1.5.2]pentadecan-15-one or 7,14-diazadispiro[5.1.5.2]pentadecane-15-thione having the formula

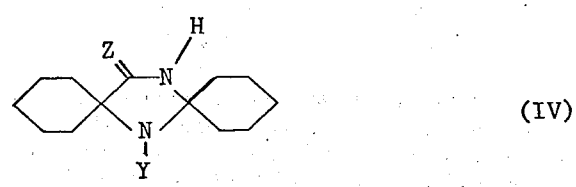

(IV)

wherein Z and y have their previous significance with an isocyanate having the formula $R_1 (NCO)_n$                   (V)

wherein $R_1$ and $n$ have their previous significance.

The reaction may be conveniently effected in a solvent which is inert towards the reactants, for instance, benzene, toluene, cyclohexane or dimethylformamide, optionally in the presence of a strong base such as 1,4-diazabicyclo[2.2.2]octane. The reaction may be carried out at the reflux temperature of the mixture, although lower reaction temperatures can be used if desired.

The present invention also provides a second, less preferred process in which a compound of formula I is produced, comprising reacting a compound having the formula (IV) as defined above with phosgene, to produce a compound of formula

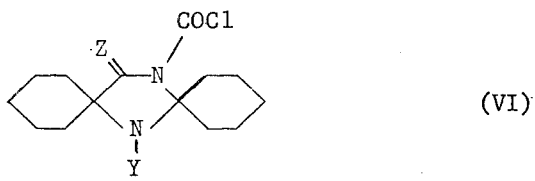

wherein Y and Z have their previous significance, which is then reacted with an amine $R_1(NH_2)_n$ wherein $R_1$ and $n$ have their previous significance. Preferably the reaction is effected in a solvent inert towards the reactants.

The present invention provides a further process for producing a compound of formula I wherein Y is other than hydrogen, comprising reacting the corresponding compound of formula I wherein Y is hydrogen with a compound capable of replacing the hydrogen at the nitrogen atom by the group Y.

For example, the nitrogen substitution reactions may be effected using an alkylating agent such as an alkyl halide.

Alternatively, the nitrogen substitution reactions may be carried out by a Leuckart or Wallach reaction using formic acid and the appropriate aldehyde or ketone. For example, the corresponding NH compound may be reacted with formic acid and formaldehyde to produce the N-methyl compound.

To produce a compound of formula I wherein Y is O, the corresponding compound of formula I wherein Y is hydrogen may be oxidised with a peroxide, such as hydrogen peroxide, optionally in the presence of pertungstic acid, or with a per-acid such as performic or peracetic acid. In a modification of this oxidation reaction, the starting material may be the corresponding N-lower alkyl compound rather than the NH compound of formula I.

The compound of formula (IV) are already known and may be prepared according to methods described in literature, i.e. W. E. Noland, R. J. Sundberg and M. L. Michaelson Journal of Organic Chemistry 28 3576 (1963) (when Z is O) and J. D. Christian Journal of Organic Chemistry 22 296 (1957) and F. Asinger et al. Monatshefte fur Chemie 98 (5) 1832 (1967) (when Z is S).

The present invention further provides a composition comprising an organic material and, a stabilising proportion of a compound of formula I as hereinbefore defined.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethylpentene-1, and also co- and terpolymers of olefines, particularly of ethylene or propylene.

Other organic materials susceptible to degradation by the effects of light and the properties of which are improved by the incorporation therein of a compound of formula I include natural and synthetic polymeric materials, for instance natural and synthetic rubbers, the latter including, for example, homo-, co- and terpolymers of acrylontrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethylacrylate; polyamides; urea-formaldehyde and melamine-formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purpose it is sufficient to use an amount of the compound of formula I within the range of from 0.01 to 5% by weight, more preferably within the range of from 0.1 to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol ethanol or acetone to powdered polymer and the whole mixed intimately in a mixer; and the solvent subsequently removed. As a further alternative the compound of formula I may be added to the polymer during the preparation of the latter, for instance at the latex stage of polymer production, to provide a pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, pasticizers, lubricants, emulsifiers, anti-static agents, flame-protectants, pigments carbon black, asbestos, glass-fibres, kaolin and talc.

The present invention therefore includes binary, tertiary and multi-component compositions containing, as stabiliser, a compound of formula I together with one or more functional additives for polymers.

Examples of suitable antioxidants are those of the hindered phenol type such as those selected from the following groups:

(1) Phenolic compounds having the general formula

wherein
Q is

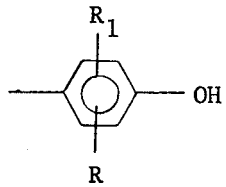

$A_1$ is $-CR(COOR'')_2$ or

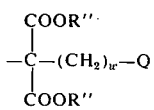

R is hydrogen or alkyl or 1 to 6 carbon atoms
R' is alkyl of 1 to 6 carbon atoms
R'' is an alkyl group having from 6 to 24 carbon atoms and
w is 0 or an integer from 1 to 4.

Illustrative examples of the compounds shown above are:
di-n-octadecyl-α-(3,5-di-t-butyl-4-hydroxy-benzyl)-malonate,
di-n-octadecyl-α-(3-t-butyl-4-hydroxy-5-methyl-benzyl)malonate which is disclosed in the Netherlands Pat. No. 6,711,199.
di-n-octadecyl-α,α'bis-(3-t-butyl-4-hydroxy-5-methyl-benzyl)malonate which is disclosed in the Netherlands Pat. No. 6,803,498.

(2) Phenolic compounds having the general formula $$Q - R'''$$

wherein Q is as hereinbefore defined and R''' is a monovalent residue derived from an aliphatic hydrocarbon having from 1 to 30 carbon atoms.

Illustrative examples of the compounds shown above are:
2,6-di-t-butyl-p-cresol
2-methyl-4,6-di-t-butylphenol and
2,6-di-octadecyl-p-cresol (3) Phenolic compounds having the formula $$Q-C_wH_{2w}-Q$$

wherein Q and x are as hereinbefore defined.
Illustrative examples of the compound shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4-(2-butylidene)-bis(2-t-butyl-5-methylphenol)
2,2'-methylene-bis(3-t-butyl-5-ethylphenol)
4,4'-methylene-bis(3,5-di-t-butylphenol)
4,4'-methylene-bis(3-t-butyl-5-methylphenol) and
2,2'-methylene-bis(3-t-butyl-5-methylphenol).

(4) Phenolic compounds having the formula $$R'''-O-Q$$

wherein Q and R''' are as hereinbefore defined.

Illustrative examples of such compounds are:
2,5-di-t-butylhydroquinone
2,6-di-t-butylhydroquinone
2,5-di-t-butyl-4-hydroxyanisole (5) Phenolic compounds having the formula $$Q-S-Q$$

wherein Q is as hereinbefore defined.
Illustrative examples of such compounds are:
4,4'-thiobis-(2-t-butyl-5-methylphenol)
4,4'-thiobis-(2-t-butyl-6-methylphenol)
2,2'-thiobis-(6-t-butyl-4-methylphenol) and
4,4'-thiobis-(2-methyl-5-t-butylphenol)

(6) Phenolic compound having the formula

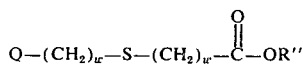

wherein Q, R'' and w are as hereinbefore defined.
Illustrative examples of such compounds are:
octadecyl-(3,5-dimethyl-4-hydroxybenzylthio)-acetate and
dodecyl-(3,5-di-t-butyl-4-hydroxybenzylthio)-propionate (7) Phenolic compounds having the formula

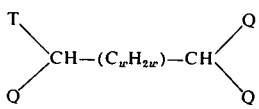

wherein T is hydrogen or Q, and w and Q are as hereinbefore defined.
Illustrative examples of such compounds are:
1,1,3-tris(3,5-dimethyl-4-hydroxyphenyl)-propane
1,1,3-tris(5-t-butyl-4-hydroxy-2-methylphenyl)-butane and
1,1,5,5-tetrakis-(3'-t-butyl-4'-hydroxy-6'-methylphenyl)n-pentane (8) Phenolic compounds having the formula

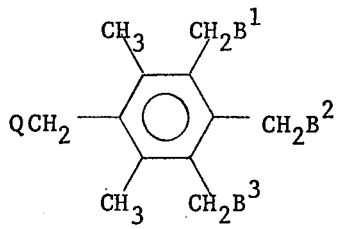

wherein $B^1$, $B^2$ and $B^3$ are each independently hydrogen, methyl or Q, provided that when $B^1$ and $B^3$ are Q then $B^2$ is hydrogen or methyl and when $B^2$ is Q then $B^1$ and $B^3$ are each independently hydrogen or methyl, and Q is as hereinbefore defined.

Illustrative examples of such compounds are:
1,4-di(3,5-di-t-butyl-4-hydroxybenzyl)-2,3,5,6-tetramethylbenzene and
1,3,5-tri(3,5-di-t-butyl-4-hydroxybenzyl)-2,4,6-trimethylbenzene (9) Phenolic compound having the formula

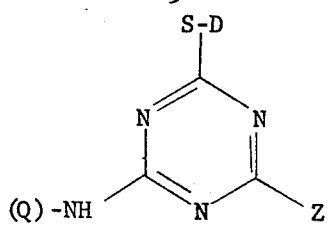

wherein Z is NHQ, —S—D— or —O—Q, D is an alkyl group having from 4 to 18 carbon atoms or —($C_wH_{2-w}$)—S—R″ and Q, R″ and w are as hereinbefore defined.

Illustrative examples of such compounds are:
2,4-bis-(n-octylthio)-6-(3,5-di-t-butyl-4-hydroxyaniline)-1,3,5-triazine
6-(4-hydroxy-3-methyl-5-t-butylanilino)-2,4-bis(n-octylthio)-1,3,5-triazine
6-(4-hydroxy-3,5-dimethylanilino)-2,4-bis-(n-octylthio)-1,3,5-triazine
6-(4-hydroxy-3,5-di-t-butylanilino)-4-(4-hydroxy-3,5-di-t-butylphenoxy)-2-(n-octylthio)-1,3,5-triazine
2,4-bis(4-hydroxy-3,5-di-t-butylanilino)-6-(n-octylthio)-1,3,5-triazine The above phenolic triazine stabilizers are more fully described in U.S. Pat. No. 3,255,191.

(10) Phenolic compounds having the formula

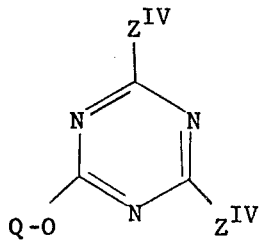

wherein each $Z^{IV}$ is the same or different and is —O—Q, —S—D or —S—($C_wH_{2w}$)—SD; and Q, D and W are as hereinbefore defined.

Illustrative examples of such compounds are:
2,4-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

The above phenolic triazine stablizers are more fully described in U.S. Pat. No. 3,255,191.

(II) Phenolic compounds having the formula $[Q—C_zH_{2z}—COO—C_zH_{2z}]_p—R^{IV}—(R)_{4-p}$ wherein p is an integer from 2 to 4, $R^{IV}$ is a tetravalent radical derived from an aliphatic hydrocarbon having from 1 to 30 carbon atoms, an aliphatic mono- or dithio ether having from 1 to 30 carbon atoms, an aliphatic mono- or diether having from 1 to 30 carbon atoms or $R^{IV}$ is hydrogen when p is 4, z is 0 or an integer from 1 to 6, and Q and R are as hereinbefore defined.

Illustrative examples of such compounds are:

Sub - class I n-Octadecyl-3-(3,5-di-t-butyl-4-hydroxyphenyl)-propionate
n-Octadecyl-2-(3,5-di-t-butyl-4-hydroxyphenyl)-acetate
n-Octadecyl-3,5-di-t-butyl-4-hydroxybenzoate
n-Hexyl-3,5-di-t-butyl-4-hydroxyphenylbenzoate
n-Dodecyl-3,5-di-t-butyl-4-hydroxy benzoate
Neo-dodecyl-3-(3,5-di-t-butyl-4-hydroxyphenyl)-propionate
Dodecyl-β-(3,5-di-t-butyl-4-hydroxyphenyl)-propionate
Ethyl-α-(4-hydroxy-3,5-di-t-butylphenyl)-isobutyrate
Octadecyl-α-(4-hydroxy-3,5-di-t-butylphenyl)-isobutyrate and
Octadecyl-α-(4-hydroxy-3,5-di-t-butylphenyl)-propionate Sub - class II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate and
2-(n-octadecylthio)ethyl 3-(3,5-di-t-butyl-4-hydroxyphenyl)propionate Sub - class III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaerythritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
1,2,3-butanetriol tris-[3-(3,5-di-t-butyl-4-hydroxyphenyl)propionate]

2-hydroxyethyl 7-(3-methyl-5-t-butyl-4-hydroxyphenyl)heptanoate and 2-stearoyloxyethyl 7-(3-methyl-5-t-butyl-4-hydroxyphenyl)heptanoate and 1,6-n-hexanediol-bis[(3',5'-di-t-butyl-4-hydroxyphenyl)propionate]

The above phenolic ester stabilizers of sub-classes I, II and III are more fully described in British patent specifications Nos. 1,103,144, 1,105,699 and 1,001,098 respectively. (12) Phenolic compounds having the formula

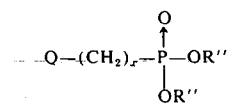

where $x$ is an integer of 1 or 2, and Q and R'' are as hereinbefore defined.

Illustrative examples of such compounds are:

Di-n-octadecyl 3,5-di-t-butyl-4-hydroxybenzyl-phosphonate

Di-n-octadecyl 3-t-butyl-4-hydroxy-5-methylbenzylphosphonate

Di-n-octadecyl 2-(3,5-di-t-butyl-4-hydroxyphenyl)-ethane-phosphonate

Di-n-tetradecyl 3,5-di-t-butyl-4-hydroxybenzylphosphonate

Di-n-hexydecyl 3,5-di-t-butyl-4-hydroxybenzylphosphonate

Di-n-docosyl-3,5-di-t-butyl-4-hydroxybenzylphosphonate and

Di-n-octadecyl 3,5-di-t-butyl-4-hydroxybenzylphosphonate.

The above si-(higher) alkyl phenolic phosphonates are more fully described in U.S. Pat. No. 3,281,505.

(13) Phenolic compounds having the formula

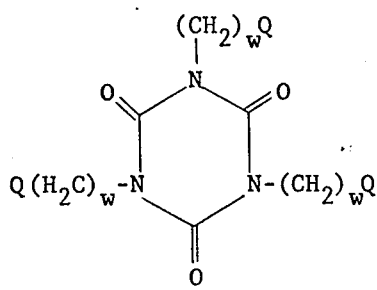

wherein $w$ and Q are as hereinbefore defined.

An illustrative example of such a compound is: tris-(3,5-di-t-butyl-4-hydroxybenzyl)isocyanurate.

The above hydroxyphenylalkyl isocyanurates are more fully described in U.S. Pat. No. 3,331,483.

The above phenolic stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:

phenyl-1-naphthylamine
phenyl-2-naphthylamine
N,N'-diphenyl-p-phenylenediamine
N,N'-di-sec.butyl-p-phenylenediamine 6-Ethoxy-2,2,4-trimethyl-1,2-dihydroquinoline
6-Dodecyl-2,2,4-trimethyl-1,2-dihydroquinoline
Mono-and di-octyliminodibenzyl and
polymerised 2,2,4-trimethyl-1,2-dihydroquinoline.

(a). 2-(2'-hydroxyphenyl)benzotriazoles, for instance 5'-methyl; 3',5'-di-t-butyl; 5'-t-butyl; 5-chloro-3',5'-di-t-butyl; 5-chloro-3'-t-butyl-5'-methyl; 3'-sec. butyl-5'-tert.butyl; 3'-[α-methylbenzyl]-5'-methyl-; 3'-[α-methylbenzyl)-5'-methyl-5-chloro-; 4-octoxy-; 3',5'-di-t-amyl; 3'-methyl-5'-carbamethoxyethyl; 5-chloro-3',5'-di-t-amyl derivatives;

(b). 2,4-bis-(2'-hydroxyphenyl)-6-alkyl-S-triazines, for instance the 6-ethyl or 6-undecyl derivatives.

c. 2-hydroxybenzophenone, for instance the 4-hydroxy, 4-methoxy, 4-octoxy-, 4-decyloxy-, 4-dodecyloxy-, 4,2', 4'-trihydroxy or 2'-hydroxy-4,4'-dimethoxy derivatives.

(d). 1,3-Bis-(2'-hydroxybenzoyl)-benzenes for instance, 1,3-bis-(2'-hydroxy-4'-hexyloxybenzoyl)-benzene 1,3-bis-(2'-hydroxy-4'-octoxybenzoyl)-benzene and 1,3-bis-(2'-hydroxy-4'-dodecyloxybenzoyl)benzene;

(e). Aryl esters or optionally substituted benzoic acids such as phenylsalicylate, octylphenylsalicylate, dibenzoyl resorcinol, bis-(4-tert.butylbenzoyl)resorcinol, o-benzoylresorcinol and 3,5-di-tert.butyl-4-hydroxy-benzoic acid 2,4-di-tert.butyl phenyl ester and octadecyl ester and -2-methyl-4,6-di-tert.butyl phenyl ester;

f. Acrylates, for instance α-Cyano-β,β-diphenylacrylic acid ethyl- or iso-octyl ester, α-carbomethoxycinnamic acid, methyl- or butyl ester and N-(β-carbomethoxyvinyl)-2-methyl indoline.

g. Nickel compounds such as nuckel complexes of 2,2'-thio-bis-(4-tert.octylphenol), for instance the 1:1 and 1:2 complexes, optionally having other ligands such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert.butylbenzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and (h). Oxalic acid diamides, for instance
4,4'-dioctyloxyoxanilide
2,2'-dioctyloxy-5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide and
mixtures of o- and p-methoxy and ethoxy-di-substituted oxanilides and the compound of formula

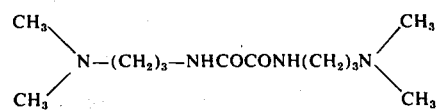

Phosphite stabilizers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-di-phosphaspiro-(5,5)-undecane and tri-(4-hydroxy-3,5-di-tert.butylphenyl)phosphite.

Peroxide-decomposing compounds for polyolefins include esters of $\beta$-thiodipropionic acids, for instance the lauryl-, stearyl-, myristyl- or tridecyl esters, salts of mercaptobenzimidazoles such as the zinc salt and di-phenylthiourea.

Suitable polyamide stabilizers include copper salts in combination with iodides and/or further phosphorus compounds and salts of bivalent manganese.

Basic co-stabilizers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilizers include organotin compounds, organo lead compounds and Ba/Cd salts of fatty acids.

Examples of nucleation agents are 4-tert.butyl benzoic acid, adipic acid and diphenylacetic acid.

As with the compound of formula I, may any further additive is advantageously employed in a proportion within the range of from 0.01 to 5% by weight, based on the weight of untreated organic materials.

In binary combinations with one or more antioxidants listed above or in ternary combinations with such antioxidants and U.V. absorbers listed above, the compounds of formula I provide very effective stabilizer packages in polyolefin formulations.

Some Examples will now be given. Parts, ratios and percentages shown therein are by weight unless otherwise stated. Parts by weight bear the same relation to parts by volume as do kilograms to liters.

EXAMPLE 1

11.1 Parts of 7,14-diazadispiro[5.1.5.2]pentadecan-15-one, 2.9 parts of methyl isocyanate and a trace of 1,4-diazabicyclo[2.2.2]octane in 80 parts of dry benzene were heated at reflux for 48 hours, cooled and filtered. The filtrate was evaporated to dryness and the residue recrystallised from ethanol, and dried in vacuo to give 9 parts of 14-methylcarbamoyl-7,14-diazadispiro[5.1.5.2]pentadecan-15-one, having a melting point of 98° to 100°C. This material gave the following elemental analysis by weight:

|  | Required for $C_{15}H_{25}N_3O_2$ | Found |
|---|---|---|
| Carbon | 64.60% | 64.64% |
| Hydrogen | 9.00% | 9.19% |
| Nitrogen | 15.00% | 15.00% |

EXAMPLE 2

5.55 Parts of 7,14-diazadispiro[5.1.5.2]pentadecan-15-one, 2.97 parts of phenyl isocyanate and a trace of 1,4-diazabicyclo[2.2.2]octane in 100 parts of dry benzene were stirred and heated at reflux for 36 hours. After removal of the benzene by distillation under reduced pressure the residue was crystallised from petroleum ether of boiling range 60–80°C to give 4.50 parts of 14-phenylcarbamoyl-7,14-diazadispiro[5.1.5.2]pentadecan-15-one having a melting point of 129° to 130°C and the following elemental analysis by weight:

|  | Required for $C_{20}H_{27}N_3O_2$ | Found |
|---|---|---|
| Carbon | 70.37% | 70.24% |
| Hydrogen | 7.97% | 8.18% |
| Nitrogen | 12.30% | 12.05% |

EXAMPLE 3

5.5 Parts of 7.14-diazadispiro[5.1.5.2]pentadecan-15-one, 2.1 parts of hexamethylene diisocyanate and a trace of 1,4-diazabicyclo[2.2.2]octane in 150 parts of dry benzene were refluxed for 48 hours. The solvent was removed in vacuo and the solid material stirred in 150 parts of water for 30 minutes. The solid was filtered and recrystallised from ethanol to give hexane-1',6'-bis[14-carbamoyl-7,14-diaza dispiro5.1.5.2]pentadecan-15-one] of melting point 164° to 165°C. This material gave the following elemental analysis by weight.

|  | Required for $C_{34}H_{56}N_6O_4$ | Found |
|---|---|---|
| Carbon | 66.67% | 66.28% |
| Hydrogen | 9.13% | 9.36% |
| Nitrogen | 13.73% | 13.32% |

EXAMPLE 4

5.5 Parts of 7,14-diazadispiro[5.1.5.2]pentadecan-15-one, 3.2 parts of n-hexylisocyanate and a trace of 1,4-diazabicyclo[2.2.2]octane in 100 parts of dry benzene were heated at reflux for 36 hours. The solvent was evaporated in vacuo and the residue stirred with 100 parts of water for 24 hours. This phase was extracted three times with 100 parts of chloroform and the extracts dried over magnesium sulphate. Evaporation of the solvent in vacuo gave an oil which was distilled at 157°C (0.3 mm pressure). This liquid, 14-n-hexylcarbamoyl-7,14-diazadispiro[5.1.5.2]pentadecan-15-one, gave the following elemental analysis by weight:

|  | Required for $C_{20}H_{35}N_3O_2$ | Found |
|---|---|---|
| Carbon | 68.73% | 68.78% |
| Hydrogen | 10.09% | 9.79% |
| Nitrogen | 12.02% | 11.91% |

EXAMPLE 5

11.1 Parts of 7,14-diazadispiro[5.1.5.2]pentadecan-15-one, 6.25 parts of 4,4'-diisocyanatodiphenylmethane and a trace of 1,4-diazabicyclo[2.2.2]octane in 125 parts of dry toluene were heated at reflux for 24 hours. After removal of the toluene by distillation under reduced pressure the residue was washed well with boiling ethyl alcohol and dried to give 9.60 parts of diphenylmethane-4',4''-bis [14-carbamoyl-7,14-diazadispiro[5.1.5.2]pentadecan-15-one] having a melting point of 217° to 220°C and the following elemental analysis by weight:

|  | Required for $C_{41}H_{54}N_6O_4$ | Found |
|---|---|---|
| Carbon | 70.83% | 70.62% |
| Hydrogen | 7.83% | 7.49% |
| Nitrogen | 12.10% | 12.10% |

EXAMPLE 6

11.1 Parts of 7,14-diazadispiro[5.1.5.2]pentadecan-15-one, 6.88 parts of cyclohexyl isocyanate and a trace of 1,4-diazabicyclo[2.2.2]octane in 150 parts of dry benzene were heated at reflux for 30 hours, cooled and filtered to remove N,N'-dicyclohexyl urea. The benzene filtrate was evaporated to dryness and the residue crystallised from petroleum ether of boiling range 80°–100°C to give 2.60 parts of 14-cyclohexylcarbamoyl-7,14-diazadispiro[5.1.5.2]pentadecan-15-one having a melting point of 106° to 109°C and the following analysis by weight:

| | Required for $C_{20}H_{33}N_3O_2$ | Found |
|---|---|---|
| Carbon | 69.10% | 69.14% |
| Hydrogen | 9.57% | 9.36% |
| Nitrogen | 12.10% | 11.91% |

EXAMPLE 7

11.1 Parts of 7,14-diazadispiro[5.1.5.2]pentadecan-15-one, 8.50 parts of 1-naphthyl isocyanate and a trace of 1,4-diazabicyclo[2.2.2]octane in 125 parts of dry toluene were heated at reflux for 24 hours. After removal of the toluene by distillation under reduced pressure the residue was twice recrystallised from benzene to give 7.0 parts of 14-naphthylcarbamoyl-7,14-diazadispiro[5.1.5.2]pentadecan-15-one having a melting point of 157° to 160°C and the following elemental analysis by weight:

| | Required for $C_{24}H_{29}N_3O_2$ | Found |
|---|---|---|
| Carbon | 73.62% | 73.58% |
| Hydrogen | 7.46% | 7.44% |
| Nitrogen | 10.74% | 10.53% |

EXAMPLE 8

4.4 Parts of 7,14-diazadispiro[5.1.5.2]pentadecan-15-one, 20 parts of allyl isocyanate and a trace of 1,4-diazabicyclo[2.2.2]octane in 100 parts of dry benzene were heated at reflux for 18 hours. The solvent was evaporated in vacuo and the residue was stirred in 100 parts of water for 12 hours. This phase was extracted with chloroform and the extracts washed with brine and dried over magnesium sulphate. Evaporation of the solvent in vacuo afforded an oil which was chromatographed on an alumina column to give 14-allylcarbamoyl-7,14-diazadispiro[5.1.5.2]pentadecan-15-one which gave the following elemental analysis by weight:

| | Required for $C_{17}H_{27}N_3O_2$ | Found |
|---|---|---|
| Carbon | 66.85% | 66.55% |
| Hydrogen | 8.91% | 8.88% |
| Nitrogen | 13.76% | 13.64% |

EXAMPLE 9

5.5 Parts of 7,14-diazadispiro[5.1.5.2]pentadecan-15-one, 1.76 parts of ethyl isocyanate and a trace of 1,4-diaza bicyclo[2.2.2]octane in 100 parts of dry benzene were heated at reflux for 18 hours. The solvent was evaporated in vacuo and the residue was stirred in 100 of water for 6 hours. 6.4 Parts of a solid were separated by filtration and crystallised twice from ethanol to yield 14-ethylcarbamoyl-7,14-diazadispiro[5.1.5.2]pentadecan-15-one as colourless crystals of melting point 185° to 188°C. This material gave the following elemental analysis by weight:

| | Required for $C_{16}H_{27}N_3O_2$ | Found |
|---|---|---|
| Carbon | 65.50% | 65.28% |
| Hydrogen | 9.28% | 9.03% |

EXAMPLE 10

3.33 Parts of 7,14-diazadispiro[5.1.5.2]pentadecan-15-one, 2.19 parts of p-tolylisocyanate and a trace of 1,4-diazabicyclo[2.2.2]octane in 150 parts of dry benzene were heated at reflux for 24 hours. The solvent was evaporated in vacuo to yield a solid material which was recrystallised from ethanol to give 4.2 parts of 14-p-tolylcarbamoyl-7,14-diazadispiro[5.1.5.2]pentadecan-15-one as colourless crystals of melting point 136° to 138°C. This material gave the following elemental analysis by weight:

| | Required for $C_{21}H_{29}N_3O_2$ | Found |
|---|---|---|
| Carbon | 70.96% | 71.10% |
| Hydrogen | 8.22% | 7.96% |
| Nitrogen | 11.82% | 11.56% |

EXAMPLE 11

5.5 Parts of 7,14-diazadispiro[5.1.5.2]pentadecan-15-one, 3.84 parts of p-chlorophenyl isocyanate and a trace of 1,4-diazabicyclo[2.2.2]octane in 100 parts of dry benzene were heated at reflux for 36 hours. The solvent was removed in vacuo to yield a solid material which was recrystallised twice from petroleum ether of boiling range 60° to 80°C affording 5.6 parts of 14-p-chlorophenylcarbamoyl-7,14-diazadispiro[5.1.5.2-]pentadecan-15-one as colourless needles of melting point 139° to 141°C. This material gave the following elemental analysis by weight:

| | Required for $C_{20}H_{26}N_3O_2Cl$ | Found |
|---|---|---|
| Carbon | 63.91% | 63.85% |
| Hydrogen | 6.92 | 7.21% |
| Nitrogen | 11.19% | 11.10% |

EXAMPLE 12

5.5 Parts of 7,14-diazadispiro[5.1.5.2]pentadecan-15-one, 7.4 parts of n-octadecylisocyanate and a trace of 1,4-diazabicyclo[2.2.2]octane in 100 parts of dry benzene were heated at reflux for 36 hours. The solvent was evaporated in vacuo and the residue sublimed in vacuo to remove unreacted lactam. The residue was then dissolved in 100 parts of ether and treated with gaseous hydrogen chloride. A colourless solid was collected by filtration and dried in vacuo. This material, 14-n-octadecylcarbamoyl-7,14-diazadispiro[5.1.5.2-]pentadecan-15-one hydrochloric acid salt, had a melting point of 121.5° to 123.5°C and gave the following elemental analysis by weight:

| | Required for $C_{32}H_{59}N_3O_2HCl$ | Found |
|---|---|---|
| Carbon | 69.38% | 68.97% |
| Hydrogen | 10.84% | 11.07% |
| Nitrogen | 7.59% | 7.46% |
| Chlorine | 6.41% | 6.67% |

EXAMPLE 13

3.57 Parts of 7,14-diazadispiro[5.1.5.2]pentadecan-15-one, 1.95 parts of phenyl isocyanate and a trace of 1,4-diazabicyclo[2.2.2]octane in 90 parts of dry benzene were heated at reflux for 18 hours. The solvent was evaporated in vacuo and the residue was recrystallised twice from ethyl acetate to give 3.9 parts of 14-phenylcarbamoyl-7,14-diazadispiro[5.1.5.2]pentadecan-15-thione as a colourless solid of melting point 143° to 144.5°C. This material gave the following elemental analysis by weight:

|  | Required for $C_{20}H_{27}N_3OS$ | Found |
|---|---|---|
| Carbon | 67.19% | 67.35% |
| Hydrogen | 7.61% | 7.33% |
| Nitrogen | 11.76% | 11.59% |

EXAMPLE 14

3.6 Parts of 7-oxyl-7,14-diazadispiro[5.1.5.2]pentadecan-15-one (prepared from 7,14-diazadispiro[5.1.5.2]pentadecan-15-one by oxidation with hydrogen peroxide and sodium tungstate), 2.1 parts of phenyl isocyanate and a trace of 1,4-diazabicyclo[2.2.2]octane in 75 parts of dry benzene were heated at reflux for 18 hours. The solvent was evaporated in vacuo and the residue allowed to stand in 100 parts of water for 18 hours. The mixture was extracted thoroughly with chloroform and the extract washed with brine and dried over magnesium sulphate. Evaporation in vacuo afforded a solid material which was chromatographed on an alumina column to yield 7-oxyl-14-phenylcarbamoyl-7,14-diazadispiro[5.1.5.2]-pentadecan-15-one as pale red crystals of melting point 125° to 128°C. This material had the following elemental analysis by weight:

|  | Required for $C_{20}H_{26}N_3O_3$ | Found |
|---|---|---|
| Carbon | 67.36% | 67.42% |
| Hydrogen | 7.35% | 7.53% |
| Nitrogen | 11.78% | 11.54% |

EXAMPLES 15 to 19

Testing in polypropylene film

38 Parts of polypropylene were homogenised with 0.076 parts of n-octadecyl-β(4'-hydroxy-3',5'-t-butylphenyl) propionate in a kneading machine over a period of 3 minutes at 200°C. 0.19 Parts of the product of Example 1 was then added and homogenisation continued for another 7 minutes.

This composition was compression moulded into films of 0.1 mm thickness at 260°C for 6 minutes and the films so obtained were then quenched in cold water.

A section measuring 44 × 100 mm was separated from the 0.1 mm annealed polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3,100 Angstrom units; the blacklight lamps were 2 feet long, 20-watt ultraviolet lamps characterised by a peak emission of 3,500 Angstrom units. The sample was rotated concentrically about the bank of lamps so that the radiation therefrom was uniformly distributed over the section under test.

The exposed sample was examined periodically and portions of it tested for the percent/elongation at break, the time at which the sample reached 50% of the initial elongation at break was noted.

Similar tests were carrier out on polypropylene samples containing, instead of the product of Example 1, the product of Example 3, 5, 6 or 7 respectively. The results obtained are summarised in the following Table.

TABLE

| Example | Additive | Factor: Time to 50% if initial elongation at break (additive) / Time to 50% of initial elongation at break (control) |
|---|---|---|
| 19 | Product of Example 1 | 3.8 |
| 15 | Product of Example 3 | 3.1 |
| 16 | Product of Example 5 | 2.2 |
| 17 | Product of Example 6 | 3.8 |
| 18 | Product of Example 7 | 1.5 |

EXAMPLE 20

4.8 Parts of 7,14-diazadispiro[5.1.5.2]pentadecane-15-thione, 2.28 parts of methyl isocyanate and a trace of 1,4-diazabicyclo[2.2.2]octane in 100 parts of dry benzene were heated at reflux for 4 days. A further 2.28 parts of methyl isocyanate were added and the solution again heated at reflux for 16 hours. The solvent was then evaporated in vacuo and the residue was crystallised twice from ethyl acetate to give 14-methylcarbamoyl-7,14-diazadispiro[5.1.5.2]pentadecane-15-thione as a colourless solid of melting point 127° to 129°C. This material gave the following elemental analysis by weight:

|  | Required for $C_{15}H_{25}N_3OS$ | Found |
|---|---|---|
| Carbon | 60.99% | 60.80% |
| Hydrogen | 8.53% | 8.36% |
| Nitrogen | 14.19% | 13.77% |

EXAMPLE 21

4.44 Parts of 7,14-diazadispiro[5.1.5.2]pentadecan-15-one, 2.2 parts of 2,2,4-trimethylhexamethylene-1,6-diisocyanate, 0.2 parts of sodium cyanide and a trace of 1,4-diazabicyclo[2.2.2]octane in 100 parts of dry toluene were heated at reflux for 48 hours. Evaporation in vacuo afforded a solid material which was purified by chromatography (alumina) to give 2',2',4'-trimethyl hexylene-1',6'-bis[14-carbamoyl-7,14-diazadispiro[5.1.5.2]pentadecan-15-one] as a colourless solid of melting point 54° to 57°C. Structure identification was confirmed by mass spectrometry; m/e 655, 654, 530, 516, 488, 487, 474, 433, 432, 377, 376, 336, 335, 334, 249, 222, 193, 179.

EXAMPLE 22

4.8 Parts of 7,14-diazadispiro[5.1.5.2]pentadecane-15-thione, 2.92 parts of p-tolyl isocyanate, 0.2 parts of potassium cyanide and a trace of 1,4-diazabicyclo[2.2.2]octane in 100 parts of dry benzene were heated at reflux for 24 hours. The solvent was then evaporated off in vacuo and the residue treated with excess water and allowed to stand for 24 hours. The solution was extracted with chloroform and the axtracts dried and evaporated in vacuo. The residue was crystallised from ethanol to yield 5.4 parts of 14-p-tolylcarbamoyl-7,14-diazadispiro[5.1.5.2]pentadecane-15-thione as a colourless solid of melting point 127° to 129°C. This material gave the following elemental analysis by weight:

|  | Required for $C_{21}H_{29}N_3OS$ | Found |
|---|---|---|
| Carbon | 67.90% | 67.84% |
| Hydrogen | 7.87% | 8.08% |
| Nitrogen | 11.31% | 11.13% |

EXAMPLE 23

4.8 Parts of 7,14-diazadispiro[5.1.5.2]pentadecane-15-thione, 2.6 parts of n-hexyl isocyanate, 0.2 parts of potassium cyanide and a trace of 1,4-diazabicyclo[2.2.-2]octane in 100 parts of dry benzene were heated at reflux for 48 hours. The solution was treated as in Example 22 to yield 8.0 parts of a yellow oil which was purified by column chromatography (silica gel) to yield 5.33 parts of 14-n-hexylcarbamoyl-7,14-diazadispiro[5.1.5.2]pentadecane-15-thione as a heavy oil. This material gave the following elemental analysis by weight:

|  | Required for $C_{20}H_{35}N_3OS.H_2O$ | Found |
|---|---|---|
| Carbon | 62.63% | 62.65% |
| Hydrogen | 9.72% | 9.44% |
| Nitrogen | 10.96% | 10.72% |

EXAMPLE 24

4.44 Parts of 7,14-diazadispiro[5.1.5.2]pentadecan-15-one, 3.26 parts of 3,3'-dimethoxy-4,4'-biphenyl-diisocyanate, 0.2 parts of potassium cyanide and a trace of 1,4-diazabicyclo[2.2.2]octane in 100 parts dry toluene were heated at reflux with stirring for 72 hours. The solid material was then filtered and the filtrate evaporated in vacuo to yield a heavy oil which shortly solidified. This substance was purified by dry column chromatography (alumina) to yield 3,3'-dimethoxybiphenylyl-4,4'-bis[14-carbamoyl-7,14-diazadispiro[5.1.5.2]pentadecan-15-one] as a pale yellow solid of melting point greater than 250°C. This material gave the following elemental analysis by weight:

|  | Required for $C_{42}H_{56}N_6O_6$ | Found |
|---|---|---|
| Carbon | 68.09% | 67.71% |
| Hydrogen | 7.62% | 7.96% |

EXAMPLE 25

258.9 Parts of 2,2,6,6-tetramethylpiperidin-4-ol, 540 parts of bromohexane and 1000 parts of acetonitrile were heated at reflux for 72 hours. After cooling the solid was filtered off and the filtrate evaporated in vacuo to yield a semi-solid material. Addition of petroleum ether of boiling range 40° to 60°C gave further precipitation and the solution was filtered once more. Evaporation in vacuo of the filtrate gave a liquid which was distilled at 116°C/0.1 mm to give 106.1 parts of 1-n-hexyl-2,2,6,6-tetramethylpiperidin-4-ol. This material gave the following elemental analysis by weight:

|  | Required for $C_{15}H_{31}NO$ | Found |
|---|---|---|
| Carbon | 74.63% | 74.65% |
| Hydrogen | 12.94% | 12.59% |
| Nitrogen | 5.80% | 5.48% |

I claim:
1. A compound having the formula

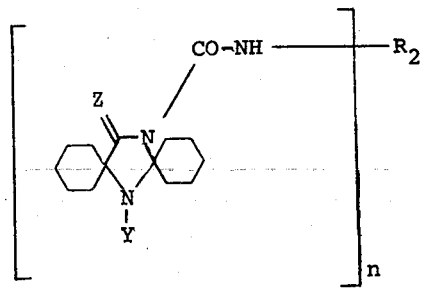

wherein $n$ is 1 or 2, Y is O, hydrogen or a straight- or branched chain alkyl group having from 1 to 4 carbon atoms Z is O or S and when $n$ is 1, $R_1$ is a straight or branched chain alkyl residue having from 1 to 20 carbon atoms; a straight- or branched chain alkenyl residue having from 3 to 18 carbon atoms; a cycloalkyl group having 5 to 14 carbon atoms or said cycloalkyl group substituted by alkyl having 1 to 12 carbon atoms or alkoxy having 1 to 4 carbon atoms; aryl group having 6 to 10 carbon atoms or said aryl group substituted by alkyl having 1 to 12 carbon atoms, alkoxy having 1 to 4 carbon atoms or one or two chlorine atoms; or an aralkyl group having from 7 to 18 carbon atoms, and when $n$ is 2, $R_2$ is a straight or branched alkylene having from 2 to 20 carbon atoms; arylene having from 6 to 18 carbon atoms or said arylene substituted by methyl; or an aralkylene group having from 7 to 18 carbon atoms, and salts of said compounds wherein the salt is a phosphate, carbonate, sulphate, chloride, acetate, stearate, maleate, citrate, tartrate, oxalate benzoate or substituted carbamate.

2. A compound of claim 1 wherein Z is oxygen.
3. A compound of claim 2 wherein $n$ is 1, Y is hydrogen and $R_2$ is alkyl, cycloalkyl, phenyl or benzyl group.
4. A compound of claim 3 wherein $R_2$ is alkyl or aryl.
5. A compound of claim 3 wherein Y is oxygen or alkyl of 1 to 4 carbon atoms.
6. A compound of claim 1 wherein Z is sulfur.
7. A compound of claim 6 wherein $n$ is 2, Y is hydrogen and $R_2$ is alkylene of 2 to 6 carbon atoms, arylene having 6 to 12 carbon atoms or diphenylmethane.
8. A compound of claim 7 wherein Y is oxygen or alkyl of 1 to 4 carbon atoms.
9. The compound of claim 1 which is hexane-1',6'-bis[14-carbamoyl-7,14-diazadispiro[5.1.5.2]pentadecane15-one].
10. A compound as claimed in claim 1, being 14-methylcarbamoyl-7,14-diazadispiro[5.1.5.2]pentadecan-15-one.
11. A compound as claimed in claim 1, being 14-cyclohexylcarbamoyl-7,14-diazadispiro[5.1.5.2]pentadecan-15-one.

* * * * *